US012747169B2

(12) United States Patent
Bloomberg et al.

(10) Patent No.: US 12,747,169 B2
(45) Date of Patent: Sep. 29, 2026

(54) APPARATUS AND METHOD FOR DISINFECTING FLUIDS

(71) Applicant: Hiigenz LLC, Middletown, NJ (US)

(72) Inventors: Michael Bloomberg, Yonkers, NY (US); Daniel Guttman, Westfield, NJ (US)

(73) Assignee: Hiigenz LLC, Middletown, NJ (US)

( * ) Notice: Subject to any disclaimer, the term of this patent is extended or adjusted under 35 U.S.C. 154(b) by 0 days.

(21) Appl. No.: 18/743,268

(22) Filed: Jun. 14, 2024

(65) Prior Publication Data

US 2024/0400420 A1 Dec. 5, 2024

Related U.S. Application Data

(63) Continuation of application No. 18/325,031, filed on May 29, 2023, now Pat. No. 12,012,340.

(51) Int. Cl.

| | |
|---|---|
| ***A61L 2/00*** | (2006.01) |
| ***A61L 2/10*** | (2006.01) |
| ***A61L 2/22*** | (2006.01) |
| ***A61L 2/24*** | (2006.01) |
| ***A61L 9/14*** | (2006.01) |
| ***A61L 9/20*** | (2006.01) |
| ***B01D 17/06*** | (2006.01) |

(Continued)

(52) U.S. Cl.

CPC ................ *C02F 1/325* (2013.01); *A61L 2/10* (2013.01); *A61L 2/22* (2013.01); *A61L 2/24* (2013.01); *A61L 9/14* (2013.01); *A61L 9/20* (2013.01); *C02F 1/50* (2013.01); *A61L 2202/11* (2013.01); *A61L 2202/122* (2013.01); *A61L 2202/14* (2013.01); *A61L 2202/15* (2013.01); *A61L 2209/11* (2013.01); *A61L 2209/12* (2013.01); *A61L 2209/134* (2013.01); *C02F 2103/002* (2013.01); *C02F 2201/3222* (2013.01); *C02F 2201/324* (2013.01); *C02F 2201/326* (2013.01); *C02F 2303/04* (2013.01)

(58) Field of Classification Search

CPC ..... B08B 3/00; B08B 3/02; C02F 1/32; C02F 1/325; C02F 1/50; A61L 2/10; A61L 2/24; A61L 9/20; A61L 9/14; A61L 2/22

USPC ................. 422/3, 24, 62, 105, 186.3; 134/1; 210/748.13; 250/455.11, 453.11, 492.1, 250/493.1, 494.1

See application file for complete search history.

(56) References Cited

U.S. PATENT DOCUMENTS 6,972,415 B2 * 12/2005 Schaible .................. A61L 9/20 210/748.11

* cited by examiner

*Primary Examiner* — Monzer R Chorbaji
(74) *Attorney, Agent, or Firm* — Brian K. Johnson, Esq., LLC

(57) ABSTRACT

A disinfection apparatus and method is provided for disinfecting a fluid. The apparatus elements define three internal container volumes. Fluid is introduced into an entry volume where its flow is conditioned to reduce splash and slow the fluid flow. The fluid is then channeled into a disinfection volume where a disinfection unit delivers a disinfection agent to the fluid. Finally, the fluid exits the apparatus through an exit volume. In one aspect, a sink-trap is disclosed in which wastewater liquid contacts a pair of diverters. The diverters have conditioned contact surfaces that slows and spreads the liquid flow and reduces liquid splash. The wastewater then passes through a UV chamber in which it is disinfected. The liquid then exits the sink-trap. Advanced self-cleaning apparatus are additionally disclosed to clean and disinfect the sink-trap and trapped wastewater. The entire apparatus operates under computer control.

20 Claims, 6 Drawing Sheets

(51) Int. Cl.
*B08B 3/12* (2006.01)
*C02F 1/32* (2023.01)
*C02F 1/50* (2023.01)
*G01N 21/00* (2006.01)
*C02F 103/00* (2006.01)

APPARATUS AND METHOD FOR DISINFECTING FLUIDS

CROSS-REFERENCE TO RELATED APPLICATIONS

This application is a continuation of and claims priority to U.S. patent application Ser. No. 18/325,031 titled "Apparatus and Method for Disinfecting Fluids" filed May 29, 2023, which in turn claims priority to U.S. patent application Ser. No. 17/449,801 titled "Apparatus and Method for Disinfecting Fluids" filed Oct. 1, 2021, which in turn claims priority to U.S. Provisional Patent Application Ser. No. 63/086,125, titled "Method and Apparatus for Sink Sterilization," filed on Oct. 1, 2020. The entire contents of each and every one of these patent applications being incorporated by reference into the present patent application as if set forth herein in their entirety.

COPYRIGHT & TRADEMARK/TRADENAME NOTICES

Certain marks referenced herein may be common law or registered trademarks of the applicant, the assignee or third parties affiliated or unaffiliated with the applicant or the assignee. Use of these marks is for providing an enabling disclosure by way of example and shall not be construed to exclusively limit the scope of the disclosed subject matter to material associated with such marks.

BACKGROUND OF THE INVENTION

1. Field of the Invention

The invention relates to the performance and optimization of fluid disinfection. In particular, a fluid disinfection apparatus and method are provided to accurately and effectively disinfect any fluid by conditioning and channeling the fluid into a particular disinfection area, disinfecting it there and permitting the disinfected fluid to exit the apparatus. This invention has a specific application sink-traps in a plumbing system, although the concepts are applicable to any fluid flow that requires disinfection.

Healthcare associated infections (Hals) affect about 1-in-31 hospital patients in the U.S., according to the U.S. Centers for Disease Control and Prevention (CDC). Eliminating Hals is an important public health goal. This goal can be advanced by generating the scientific data that lead to "best practices" and engineering solutions that help prevent cross-contamination of hospital surfaces. Doctors, nurses, or orderlies standing at a hospital bedside have typically washed their hands prior to working with the patient. Almost all of the hospital guidelines in the developed world contain regulations and guidelines regarding medical professional handwashing and the associated use of sinks for the same. The treatment methods for input water, the ratio of sinks per beds, the placement of sinks within patient rooms etc. are all considered and regulated. In a post COVID-19 world in particular, hospitals have installed and pushed for more hand-washing stations as part of the effort to cut down on the spread of pathogens that thrive in hospitals.

However, sinks themselves have been implicated in the spread of dangerous bacteria. As a case of unintended consequences, sinks have been linked to a number of outbreaks of serious infections in numerous hospitals worldwide. In one case of remediation, a hospital in the Netherlands took sinks out of the patient rooms in its intensive care unit to slow the spread of bacteria. The results were positive. At a time when concern is mounting about antibiotic resistance, the specter of untreatable infections threatens the advances of modern medicine. Finding ways to slow the development and spread of drug-resistant bacteria is a major preoccupation of infection control teams. As a result, evidence is mounting that hospital sinks could exacerbate the problem presented to health care specialists since the sink is the cornerstone of infection control policy.

Sinks next to toilets in patient rooms may be the biggest culprits. In a recent study reported by the American Journal of Infection Control, researchers at the Medical College of Wisconsin checked a large Wisconsin hospital for *Klebsiella pneumoniae* carbapenemase (KPC). KPC is a type of bacteria that can cause health care-associated infections such as pneumonia, bloodstream infections, wound infections or surgical site infections. In that study, researchers comparison-tested ICU patient drains in sinks next to patient toilets sinks versus sinks closer to the entrance of patient rooms. KPC was found in 87 percent of patient sinks next to toilets, compared with about 22 percent of sinks near room entry doors. In 4 out of 5 rooms where KPC was found in the entry door sinks, it was also found in the sink near the toilet, suggesting a possible source of cross contamination. The research also determined that the sink drains in ICU rooms may be subject to cross-contamination from some or all of the following: (a) biofilms growing in pipes shared in common plumbing between toilets and sinks; (b) bioaerosols from toilet flushing spreading bacteria into the sinks, especially those nearest the toilet; and (c) "seeding" of bacteria from routine hand hygiene practiced by patients or healthcare workers. Biofilms are slimy coatings on wet surfaces that harbor complex microbial communities. Additional research from other studies revealed that hospital superbugs could migrate upward through drain-pipes in biofilms toward the sink strainer. Having colonized the P-shaped water trap in the plumbing under sinks, biofilms were found to grow toward the sink strainer at a rate of about one inch per day. Once in the sink strainer area, the superbugs then could be dispersed into the environment near the sink though the impact of streaming water from the faucet splashing into the sink.

Studies have also been performed regarding bacterial accumulation in electronic eye faucets—the no-tap sinks where water flow is activated by placing one's hands in front of a sensor. The expectation was that sinks without taps would actually reduce the risk that freshly washed hands would be re-contaminated by turning off taps. Some of those sinks were found to be more likely to accumulate bacteria, since they have multiple internal valves and more surfaces on which biofilms can form. The take-away is that sink designs need to be tested, in the way drugs are, to ensure they are actually sanitary.

In combination with the recent COVID-19 pandemic, these data have major implications for infection control. In particular, modified hand hygiene practices and sink disinfection protocols may be needed to stem the risk of transmission among health care providers and patients alike.

2. Description of Related Art

PCT Pat. Pub. No. WO2007/081401A2, to Optimus Services LLC (Optimus) and published Jul. 19, 2007, discloses a very simple system for disinfecting sink-trap water in an attempt to solve the above-mentioned problem. In Optimus, a method of sterilizing sink-traps is disclosed using UV radiation. The method involves a direct irradiation of the sink-trap wastewater by removing a portion of the typical trap plumbing pipe. In Optimus, sink-trap piping is modified so that a portion of the piping is cut out and removed. Transparent quartz glass windows are fitted and sealed in the openings created, thereby providing optical access to the pipe interior and the passing wastewater therein. A UV lamp source is located on the other side of the quartz glass (outside the pipe) such that the wastewater in the existing trap pipe is irradiated by the UV lamp as it passes through. Optimus apparently offers a commercial product employing the above-recited PCT Pat. Pub.

However, the Optimus system suffers from several deficiencies. Primarily, the quartz seal has to be maintained, over a presumably large seal length against a pipe that is occasionally under pressure. Further, the direct irradiation of an entire cylinder of wastewater in which that fluid cylinder is typically as wide as the piping, raises questions as to the efficiency of the disinfection. Bulk coagulant within the wastewater results in biomaterials being stacked behind one another within the pipe as the wastewater moves through it. In turn, front irradiated portions of the fluid may be disinfected, but fluid portions at the distal portions of the irradiated pipe will be blocked by the debris in the front fluid portions and will likely not receive sufficient disinfecting radiation.

Thus, a need exists in the art for an improved sink-trap that provides for wastewater disinfection at a highly efficient level. In order to achieve such efficiencies, the fluid flow in such systems requires particular conditioning, channeling, pathogen detection, and subsequent disinfecting to properly accommodate the increasingly stringent sanitary regulations and guidelines of present-day medical institutional settings.

BRIEF SUMMARY OF THE INVENTION

Accordingly, in one particularly preferred embodiment, a disinfection apparatus for disinfecting a fluid is provided, the apparatus includes: a container having a fluid entry opening and a fluid exit opening, the container having an inner volume, the inner volume including an entry volume, a disinfection volume and an exit volume, the entry volume adjacent to the fluid entry opening and the disinfection volume at a first end of the disinfection volume, the exit volume adjacent to the fluid exit opening and the disinfection volume at a second end of the disinfection volume, the fluid flowing through the container from the fluid entry opening through the entry volume to the disinfection volume at the first end thereof, the fluid flowing through the disinfection volume from the first end thereof to the second end thereof, the fluid flowing through the exit volume from the second end of the disinfection volume to the fluid exit opening; a first diverter and a second diverter, both of the diverters disposed within the entry volume of the container and coupled to the container, the first diverter disposed so as to divert at least a portion of the fluid entering the container within the entry volume towards the second diverter; a disinfection unit coupled to a side of the container, the disinfection unit including a disinfection module, a disinfection barrier and a computer coupled to the disinfection module through a control and data interface, the computer including a processor and an associated memory coupled to the processor, the processor executing program instructions within the memory to activate control signals within the control and data interface, the disinfection barrier providing an interface between the disinfection unit and the container at the disinfection volume, the interface providing access to the disinfection volume for the disinfection module, the disinfection module releasing a disinfection agent into the disinfection volume under the control of the computer, the disinfection agent disinfecting the fluid as the fluid passes through the disinfection volume.

In particular preferred variations within the apparatus the second diverter includes a diversion segment and a containment segment, the diversion segment and the containment segment defining the entry volume, the disinfection volume and the exit volume, a portion of the fluid entering the container within the entry volume being diverted by the diversion segment as it passes through the entry volume, the two fluid portions diverted by the first diverter and the diversion segment of the second diverter entering the disinfection volume at the first end thereof; the first diverter and the diversion segment of the second diverter have a coating, the coating reducing a splash of the fluid as it is diverted from each diverter; the disinfection barrier is an optical barrier, the disinfection unit includes at least one UV light, the UV radiation emitted from the UV light being the disinfection agent; and the disinfection barrier is a spray module, the disinfection unit includes a disinfectant chemical contained within the disinfection module, the disinfectant chemical being the disinfection agent.

In yet other aspects the apparatus includes a wiper assembly, the wiper assembly coupled to the container and including a blade, a blade holder coupled to the blade, an engagement mechanism and a blade advancement mechanism coupled to the blade engagement mechanism and the blade holder, the blade advancement mechanism moving the blade in a container cleaning dimension, the container cleaning dimension disposed parallel to at least one of the interface and the containment segment of the second diverter, the wiper assembly operating the blade holder with the engagement mechanism to move the blade advancement mechanism along the container cleaning dimension, the blade being in contact with and wiping the at least one of the interface and the containment segment when moved along the container cleaning direction; the blade advancement mechanism is a helix shaft screw, the blade holder coupled to a matching helix thread, the blade having a first edge and a second edge, the first edge of the blade contacting and wiping the interface, the second edge of the blade contacting and wiping the containment segment; the disinfection apparatus is a sink-trap and the fluid is wastewater from a sink, the sink coupled to the disinfection apparatus; the disinfection apparatus is an air vent and the fluid is air flow within a building; the sink has an inner sink surface, the inner sink surface includes a coating, the coating reducing a splash of the fluid as it enters the sink; the apparatus includes: a sink liner, the sink liner having a contour, the contour matching a sink contour of the sink, the sink liner made of a porous material, the porous material reducing a splash of the fluid as it enters the sink; and the apparatus includes: a set of program modules, the set of program modules containing the program instructions, the program modules controlling a set of parameters that operate the disinfection module, the set of parameters including at least one of a disinfection time, a disinfection rate, or a disinfection schedule.

In a particularly preferred method according to the present invention, a method is provided that includes the steps of introducing the fluid into the container at the entry opening and into the entry volume; diverting a portion of the fluid within the entry volume with the first diverter; diverting a portion of the fluid within the entry volume with the second diverter;

channeling the fluid into the disinfection volume with the second diverter and the disinfection barrier; executing program instructions with the processor to control the disinfection module with the computer; releasing a disinfection agent from the disinfection module, the disinfection agent being delivered through the disinfection barrier to the disinfection volume to disinfect the fluid; and introducing the fluid into the exit volume for evacuation from the container.

According to particularly preferred variations of the method, the method further includes the steps of emitting UV radiation from UV light through the optical barrier, the UV radiation being the disinfection agent; spraying the disinfectant chemical with the spray module, the disinfectant chemical being the disinfection agent; advancing the blade along the container cleaning direction using the blade advancement mechanism; contacting the at least one of the interface and the containment segment; wiping the at least one of the interface and the containment segment with the blade; reducing a splash of the fluid using the coating as the fluid is diverted with each diverter; reducing a splash of the fluid using the coating as it enters the sink; controlling a disinfection time, controlling a disinfection rate, or; controlling a disinfection schedule.

In yet another preferred embodiment, anon-transitory, machine-readable storage media is provided having executable instructions for causing a plurality of processors within a plurality of computers to perform a method of scheduling a disinfection apparatus to disinfect a fluid, the disinfection apparatus including container having a fluid entry opening and a fluid exit opening, the container having an inner volume, the inner volume including an entry volume, a disinfection volume and an exit volume, the entry volume adjacent to the fluid entry opening and the disinfection volume at a first end of the disinfection volume, the exit volume adjacent to the fluid exit opening and the disinfection volume at a second end of the disinfection volume, a first diverter and a second diverter, both of the diverters disposed within the entry volume of the container, a disinfection unit coupled to a side of the container, the disinfection unit including a disinfection module, a disinfection barrier and a computer coupled to the disinfection module through a control and data interface, the computer including a processor and an associated memory coupled to the processor, the processor executing program instructions within the memory to activate control signals within the control and data interface, the disinfection barrier providing an interface between the disinfection unit and the container at the disinfection volume, the interface providing access to the disinfection volume for the disinfection module, the machine-readable storage media having steps for performing the method of: introducing the fluid into the container at the entry opening and into the entry volume; diverting a portion of the fluid within the entry volume with the first diverter; diverting a portion of the fluid within the entry volume with the second diverter; channeling the fluid into the disinfection volume with the second diverter and the disinfection barrier; executing program instructions with the processor to control the disinfection module with the computer; releasing a disinfection agent from the disinfection module, the disinfection agent being delivered through the disinfection barrier to the disinfection volume to disinfect the fluid; and introducing the fluid into the exit volume for evacuation from the container.

The objects and features of the present invention may be applied jointly or severally in any combination or subcombination by those skilled in the art.

BRIEF DESCRIPTION OF THE SEVERAL VIEWS OF THE DRAWING(S)

Detailed embodiments of the present invention(s) are disclosed herein; however, it is to be understood that the disclosed embodiments are merely exemplary of the invention(s), which may be embodied in various forms. Therefore, specific structural and functional details disclosed herein are not to be interpreted as limiting, but merely as a basis for the claims and as a representative basis for teaching one skilled in the art to variously employ the present invention(s) in virtually any appropriately detailed structure. Further, the terms and phrases used herein are not intended to be limiting, but rather to provide an understandable description of the invention(s).

The accompanying drawings, which are incorporated in and constitute part of this specification, illustrate embodiments and/or aspects of the invention and/or disclosure, and together with the written description, these drawing serve to explain the principles of the invention. Wherever possible, the same reference numbers are used throughout the drawings to refer to the same or like elements of an embodiment. The embodiments illustrated herein are presently preferred, it being understood, however, that the invention is not limited to the precise arrangements and instrumentalities shown, in which:

DETAILED DESCRIPTION OF THE INVENTION

To facilitate a clear understanding of the present invention, illustrative examples are provided herein which describe certain aspects of the invention. However, it is to be appreciated that these illustrations are not meant to limit the scope of the invention, and they are provided herein to illustrate certain concepts associated with the invention.

The entire description below is provided in the particular context of a sink-trap in a plumbing system. However, the invention of the present application is generally applicable to any plumbing system such as toilets, showers, drinking fountains, utility sinks, faucets, outlet drains, lavatories, basins, tubs, grease traps, holding tanks used in boats and ships or any plumbing piping used in the drainage of water-based waste prior to flushing into main plumbing stacks, sewer systems and any other liquid fluid flow systems. Further, the objects of the present invention may be applied to disinfect any non-liquid systems of fluid flow such as air ducts, pressurized air compression systems etc. Finally, the invention is described in connection with a hospital setting, although the principles are applicable to all settings in which the apparatus may be installed.

Figure 1A:
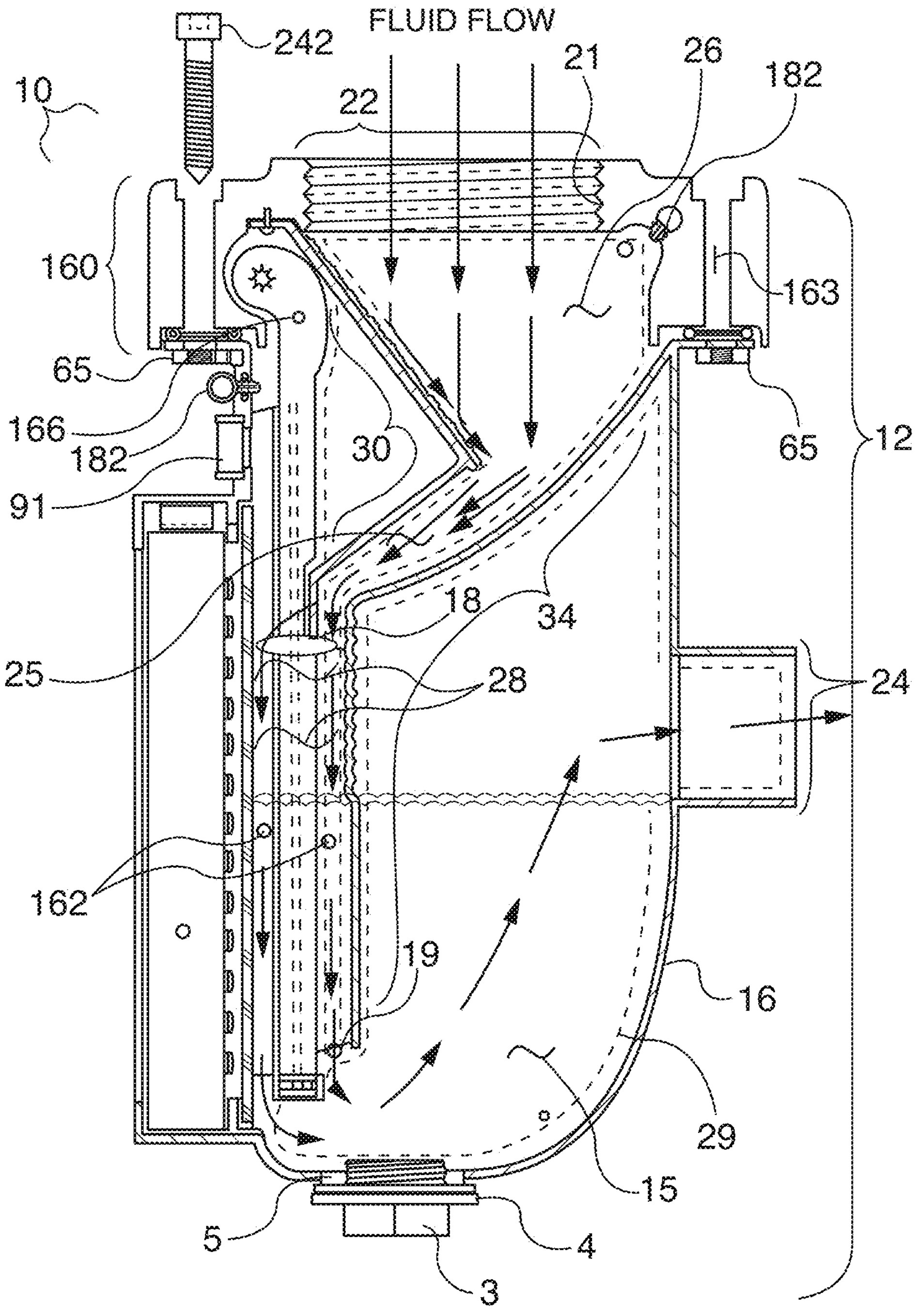
FIG. 1A shows a side sectional view of a sink-trap apparatus according to one aspect of the present invention.
Figure 1B:
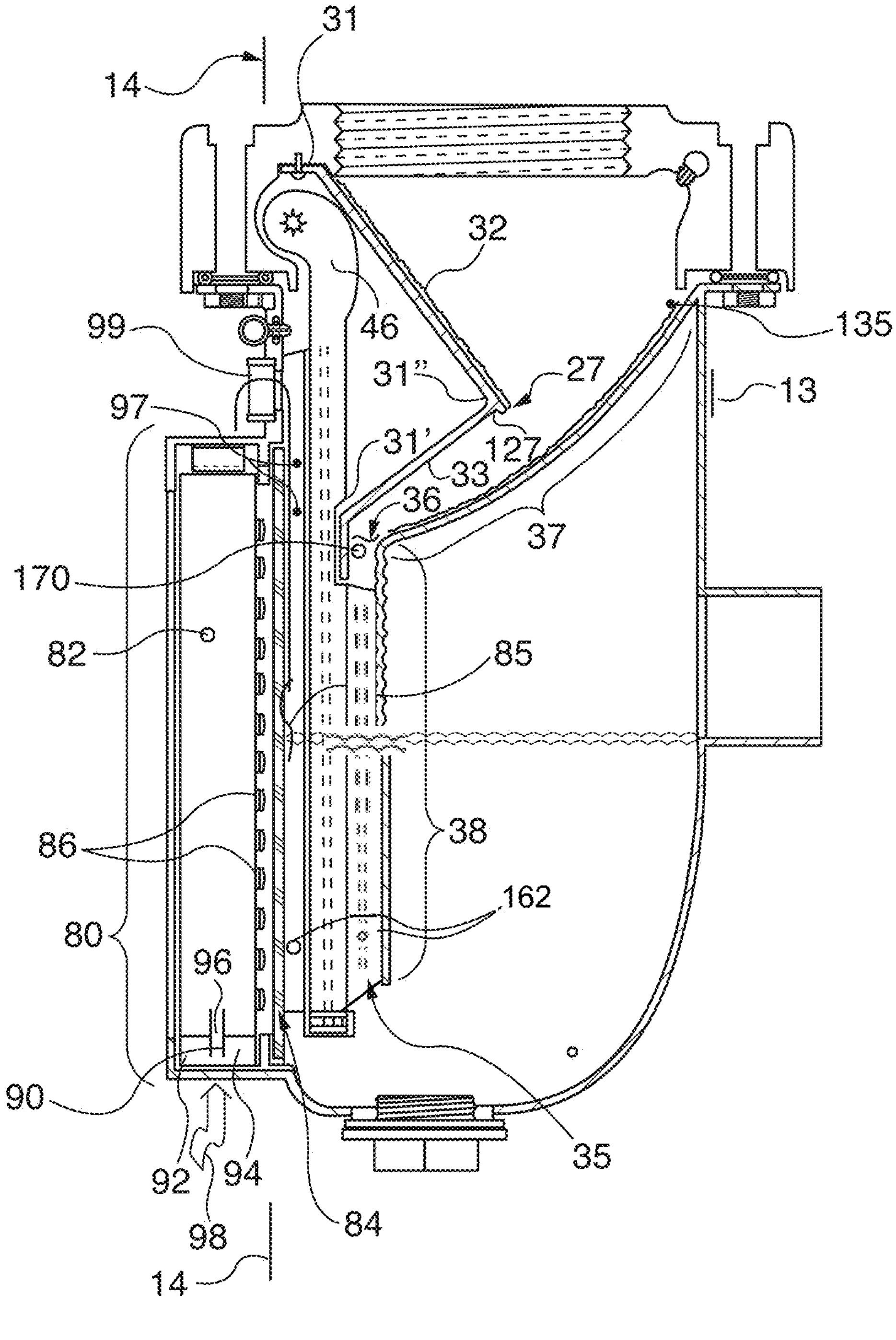
FIG. 1B shows the same side sectional view of a sink-trap apparatus as FIG. 1A illustrating other aspects of the present invention.

As shown in FIGS. 1A and 1B, disinfection apparatus 10 is provided consisting primarily of a container 12. In the context of a sink-trap, container 12 is shown as a semi-circular canister having a flat front side 14 at the container front for mounting the disinfection unit 80. Container 12 includes a fluid entry opening 22 and a fluid exit opening 24. The inner volume 15 of the entirety of the canister includes three sub-volumes: fluid entry volume 26, fluid disinfection volume 28 and fluid exit volume 29. The three sub-volumes are separated and defined by second diverter 34. Second diverter 34 includes two different segments: diversion segment 37 and containment segment 38. Diversion segment 37 is coupled to the container back side 13 (fluid exit side). Diversion segment 37 is curved in shape and extends in a concave, downward scooping arrangement towards the container front side 14. Diversion segment 37 transitions to the containment segment 38 at transition point 36. Containment segment 38 begins at transition point 36 on second diverter 34 and is disposed parallel to the container front side 14 and interface 85. Containment segment 38 extends from the transition point 36 to a termination point 35. Containment segment 38 may be coupled to the container front side 14. Both the diversion segment 37 and containment segment 38 of the second diverter 34 extend across the container cleaning dimension 169 of container 12 and are coupled to and sealed with respect to the side walls thereof.

By virtue of the positioning of second diverter 34 the three sub-volumes within container 12 are generally defined as follows. Fluid entry volume 26 is the volume within container 12 above diversion segment 37 and extending up to fluid entry opening 22. By virtue of the affixation and sealing of diversion segment 37 along all edges thereof to container 12, except at the transition point 36, the fluid entry volume 26 is "fluid-tight" and all the fluid entering container 12 will necessarily proceed through the fluid entry volume 26 and on to transition point 36. Fluid entry volume 26 borders disinfection volume 28 at or just beyond transition point 36, specifically at a first end 18 of the disinfection volume. Disinfection volume 28 extends down container 12 between container front side 14/interface 85 and the second diverter, containment segment 38. Disinfection volume 28 ends at a second end 19 of the disinfection volume. Second end 19 may be close to or aligned with the termination point 35 of second diverter 34. By virtue of the affixation and scaling of containment segment 38 along all edges thereof to container 12, except possibly at termination point 35, the disinfection volume 28 is "fluid-tight" and all the fluid entering container 12 and passing through fluid entry volume 26 will necessarily proceed through the disinfection volume 28 from its first end 18 to its second end 19.

Fluid exit volume 29 borders disinfection volume 28 at second end 19 of the disinfection volume. Fluid exit volume 29 extends down slightly into container 12 and then over-up and throughout the remaining inner volume 15 of container 12—i.e. the volume below second diverter 34. Fluid exit volume 29 ends at fluid exit opening 24. By virtue of the affixation and sealing of second diverter 34 along all edges thereof to container 12, except possibly at termination point 35, the fluid exit volume 29 is "fluid-tight" and all the fluid entering container 12 and passing through fluid entry volume 26 and disinfection volume 28 will necessarily proceed through the fluid exit volume 29 and out container 12 at fluid exit opening 24.

In the case where disinfection apparatus 10 is a sink-trap, the trap fluid may exit simultaneously in both the disinfection volume 28 and the fluid exit volume 29. These two fluid portions creates the "trap" effect of a typical plumbing system with the portion of the fluid in the fluid exit volume 29 acting as the trap seal for the sink-trap.

Referring to FIG. 1B, a first diverter 30 is disposed within the fluid entry volume 26 and affixed to the sides or top of container 12. First diverter 30 optionally includes two segments: diversion segment 32 and containment segment 33. First diverter, diversion segment 32 extends from a first diverter affixation point 31 downward into fluid entry volume 26. First diverter, diversion segment 32 desirably extends at least halfway across the fluid entry volume 26 as measured front-to-back (14 to back side 13) in container 12. Further, first diverter, diversion segment 32 desirably extends down to second diverter, diversion segment 37, but not to the point of contacting it. First diverter, diversion segment 32 ends at edge 27. First diverter, containment segment 33 extends from edge 27 and extends to second affixation point 31' at the container front side 14.

The fluid flows within container 12 in the following manner and as shown by the arrows in FIG. 1A. The fluid enters container 12 at fluid entry opening 22 and enters fluid entry volume 26. A portion of the fluid impinges upon the first diverter, diversion segment 32. Another portion of the fluid impinges upon the second diverter, diversion segment 37. Both portions of the fluid recombine within the volume between first diverter, containment segment 33 and the bottom portion of the second diverter, diversion segment 37. This volume region is the fluid combination volume 25. The fluid then flows past second diverter transition point 36 and into disinfection volume 28 at first end 18 of the disinfection volume. The fluid then progresses through disinfection volume 28 and on to the second end 19 of the disinfection volume. Finally, the fluid progresses to fluid exit volume 29 and out the container 12 through fluid exit opening 24.

Referring to FIG. 1, a container drain plug 3 is provided at the bottom of the container 12. Drain seal washer 4 is first placed over the drain plug threads and the container drain plug 3 threadably engaged with threaded drain boss 5 on container 12 to seal and secure the bottom of the container 12. Drain plug 3 may be removed to drain and clean the interior of the container 12 without disassembling the entire assembly from its mounting location.

The placement and lengths of the first and second diverters are design considerations depending on the desired fluid flow control and the need for splash control when the fluid is a liquid. The following description is provided with respect to the fluid being a liquid, although those of skill in the art will realize the appropriate alternative design considerations with respect to non-liquid fluids.

When the fluid is a liquid, and that liquid contains pathogens, fluid splash is a principal concern as it impinges on first and second diverters. It is undesirable to have the liquid impinging upon the diversion segments of the first and second diverters, only to have the liquid splash and coat the inner surfaces of the container (12) within fluid entry volume 26, or worse, splash out of the container 12 entirely through fluid entry opening 22. Two primary considerations are involved in order to accommodate desirable fluid containment and fluid flow smoothing: proper positioning and angling of the diversion segments of first and second divers; and splash mitigation of the liquid as it impinges on the two diversion segments.

To accommodate the first consideration, first diverter, diversion segment 32 should be tilted downwards at an angle that causes the liquid to stay within the container 12. This being accomplished, the next design consideration is to enable liquid hitting most portions of the first diverter, diversion segment 32 to flow down the surface of that segment without splashing. Therefore, angles, diverter lengths and material compositions should be selected to provide the smoothest fluid flow along first diverter, diversion segment 32 based on the typical impingement velocity and the fluid type. Ultimately, the portion of the liquid that first impinges first diverter, diversion segment 32 should flow down that segment and flow off of edge 27. Edge 27 can be designed as a drip edge such that the edge extends beyond mid-affixation point 31" a certain distance 127. In this arrangement, the liquid flows of the first diverter drip edge 27 onto the second diverter without flowing under the first diverter and onto the lower surface of first diverter, containment segment 33.

Liquid portions that bounce off first diverter, diversion segment 32 should be conditioned so that any splashed liquid does not splash onto the second diverter higher than splash limit point 135. This splashed portion from first diverter, diversion segment 32 then joins the portion of the liquid directly impinging on second diverter, diversion segment 37. These two liquid components then flow down second diverter, diversion segment 37, join with the "dripped" liquid component from drip edge 27, and proceed to flows down the curved surface to transition point 36. Finally, it should be noted that the curvature ratio of the second diverter, diversion segment 37 is also a design consideration in conditioning a smooth and slow liquid fluid flow through the fluid entry volume 26. In optimizing the objectives of a low splash/slow flow fluid, the exact design specifications for any particular container will likely be achieved through experimentation based on the container construction, typical fluid velocity and the actual liquid/fluid being collected.

Again, when the fluid is a liquid, an ideal apparatus would force a majority of the liquid to flow off second diverter transition point 36 and "sheet" down the front surface of second diverter, containment segment 38. Provision of a thin fluid on this surface and within the disinfection volume 28 allows for the most effective exposure and absorption of the disinfection agent 88 in this volume.

To accommodate the second consideration, minimizing splash, the previously discussed criteria are applied first: i.e. the angle, shape, construction, dimension of the first and second diversion segments 32 and 37. In addition, the impaction surface of the diversion segments of first and second diverters 32 and 37 respectively may be treated with a coating 339 that is specifically designed to reduce splash. Nanocoating these surfaces with a surfactant that breaks up and controls the splash of the impinging liquid is possible and desirable. For example, a titanium dioxide (TiO2) coating has been shown to provide such a splash response in various environments. These coatings may be applied to all or part of the liquid impaction surfaces. As with the diverter design considerations, optimization of the objectives of low splash/slow flow fluid will likely be achieved through experimentation based on the container construction, typical fluid velocity and the actual liquid/fluid being collected. Alternatively, sprayer assembly 180 may be used to inject an additive into the fluid entry volume 26 as the liquid enters that volume. As with a coating, it has been shown that by adding a viscous fluid part to the overall liquid collection taking place in the fluid entry volume, the splash of the liquid mixture impinging on the liquid impaction surfaces may be reduced. Glycerin is one splash reduction candidate. In a more sophisticated system, an aqueous solutions containing sodium dodecyl sulfate (SDS), trisiloxane molecules (TSs), and the vesicle surfactant sodium bis (2-ethylhexyl) sulfosuccinate [Aerosol OT (AOT)] may be used. In either case, the combined mixture of the liquid plus the additive creates a modified liquid with a lower splash function. Finally, to further slow the liquid fluid flow past the transition point 36, the front surface of second diverter containment segment 38 may be laser surface textured (LST) to create a laser treated surface 40. By pitting and conditioning that surface, the liquid is more likely to adhere to it, thereby slowing and evening out the progression of the liquid over that surface and through the disinfection volume 28 so as to maximize the efficiency (exposure time) of the disinfection process.

Referring to FIG. 1B, container 12 is shown with a disinfection unit 80 attached to the container front side 14. Disinfection unit 80 includes a disinfection module 82, a disinfection barrier 84 and a computer 90. The disinfection module 82 and computer 90 are disposed within the disinfection unit 80. A disinfection barrier 84 is provided at one side of the disinfection unit 80.

Disinfection barrier 84 may incorporated as a physical part of the container front side 14. The incorporation of the disinfection barrier as a part of the container front side 14 is performed such that container 12 remains "fluid tight." In this arrangement, disinfection unit 80 may be coupled to container 12 at the location of disinfection barrier 84 using any of a variety of desirable connection methodologies: slot and tab, insertion prongs, snap-on arrangements or more permanent solutions such as attachment screws. In any case and in many instances, the interface 85 will be the container-facing surface of the disinfection barrier. So for example, in the optical barrier context below the container-facing portion of the optical barrier also acts as the interface (85).

In operation, the disinfection module 82 is activated when the entire disinfection apparatus 10 is operational. As fluid flow is occurring within disinfection volume 28, disinfection module 82 is activated and disinfection agent 88 is delivered from the disinfection module 82 across the disinfection barrier to the fluid in the disinfection volume 28.

Computer 90 is included within disinfection unit 80. Computer 90 includes at least one processor and associated memory in which stored programs reside and from which the processor executes the program steps for those programs. The execution of the program steps drives the control signals 98 that cause the operations performed by the disinfection module 82 or any other computer-controlled device. The software on the mobile device may take the form of standalone software that executes solely on the computer or in the form of small program software application components (apps or applets). The computer may be accessible through a wireless connection to the computer for external control (e.g. wi-fi or Bluetooth), In any of these cases, input data on which the standalone programs or apps operate may be provided by any of a number of sources. Examples include data input by an external source such as the user of the disinfection apparatus (10) or generated from within the disinfection apparatus (10) (e.g. from sensor return signals or other signaling from computer-controlled components). These signals may be provided to the computer over the wireless or wired connection to that computer from the user or other computer controlled elements within the disinfection apparatus (10). Most relevant to the present invention, computer 90 contains a stored program, to operate the disinfection module and control the disinfection parameters used to disinfect the fluid in the disinfection volume according. In either stand-alone or app software configurations, the stored program for managing these functions is programmable, configurable and otherwise capable of being controlled by the apparatus user.

Computer 90 is coupled to disinfection module 82 through a control and data interface 96. Control and data interface 96 may be a wired or a wireless connection, but in any case, control signals 98 generated by the computer are transmitted between the computer 90 and disinfection module 82 over control and data interface 96. Additionally, sensor leads 99, attached to sensors 97 disposed within disinfection volume 28, may be included as part of the control and data interface 96. Further, external access port 91 may be included in container 12 for the insertion of sensors 97 that are externally controlled and monitored. Programmed software modules and apps may be created and stored within the computer 90 and associated memory 94 and by which processor 92 can execute programmed control over each and every portion of the apparatus capable of such control.

With respect to the disinfection volume 28, sensors 97 may be disposed within disinfection volume 28 and connected to control and data interface 96. Electronic sensors are, in general, capable of detecting and returning a plurality of data regarding the fluid being disinfected some of which include: temperature, toxicity, pH, biocontamination, salinity, liquid presence etc. This data is fed from the sensors 97 to the computer via data signals 100 over the control and data interface 96. With respect to the fluid disinfection, it is desirable to have the computer continuously monitor the status of the disinfection process. The processor can retrieve these fluid-related data from said associated memory and perform various control functions in response. In particular, disinfection schedules can be executed, i.e. controlling what times of day and when the disinfection process is executing and the disinfection agent is being released. Disinfection duration and strength are also capable of computer control, i.e. how long to release the disinfection agent during any one disinfection cycle and how much of the disinfection agent to release at any one point in time.

In one particular embodiment, the disinfection unit 80 is an optical unit, the disinfection module 82 is a UV light module having LED UV lights 86, the disinfection barrier 84 is a quartz glass window and the disinfection agent 88 is UV radiation delivered by UV lights 86. The UV light module generates control signals 98 to activate the UV lights 86, which in turn emit UV radiation. The UV radiation passes through the quartz glass window and on into the disinfection volume to disinfect the fluid therein.

UV is a well-known disinfectant for pathogens and the selection of the proper power, wavelengths and bulb size (exposure areas) are all design considerations to be selected, tested and applied in the actual practical application of the apparatus. Finally, when using UV light as the disinfection agent 88, the selection of other system components may be affected. For example, proper selection of apparatus components may be made so as to enhancement or retard UV exposure and effects. By way of example, quartz glass as the optical/disinfection barrier may be selected to provide the most optimal magnification, the best heat characteristics, the best UV band pass-through etc. Alternatively, other apparatus components such as blades 162 might be selected to be UV resistant so as to provide for better longevity.

Several physical design considerations related to safety are worth noting in the present invention. Since UV radiation is harmful to persons, care must be taken to maintain the UV within the disinfection apparatus 10, and specifically within the disinfection volume 28. First, where the disinfection module 82 is a UV lamp, the light from the UV lights 86 should emit into and be contained within disinfection volume 28. Wiper arm guide 170 may be provided along interface 85 from the end of the collection volume down into the disinfection volume so as to contain the UV in the disinfection volume 28 and prevent UV exposure within the collection volume and into the fluid entry volume. Second, the second diverter, containment segment 38 should extend sufficiently below the bottom of the disinfection module emission so as to prevent UV emission from entering the fluid exit volume. To enhance the disinfection efficacy, the front surface of containment segment 38 (or any other surface) may be coated with a reflective material so as to make the disinfection volume 28 a “light trough.” However, baffles, edges and light stops should be installed wherever necessary to maintain the “light trough” and prevent exposure outside that volume.

In another particular embodiment of the present invention, the disinfection agent is an air purifier, the fluid is air, the disinfection unit is a dispersion unit, the disinfection module 82 is a sprayer module, the disinfection barrier is row of spray nozzles and the disinfection agent is an aerosol disinfectant chemical. The disinfection module 82 generates control signals 98 to activate the spray nozzles, which in turn emit the aerosol disinfectant chemical. The aerosol disinfectant chemical passes through the spray nozzles on into entry volume 26 and on to disinfection volume 28 to disinfect the air therein.

Figure 2A:
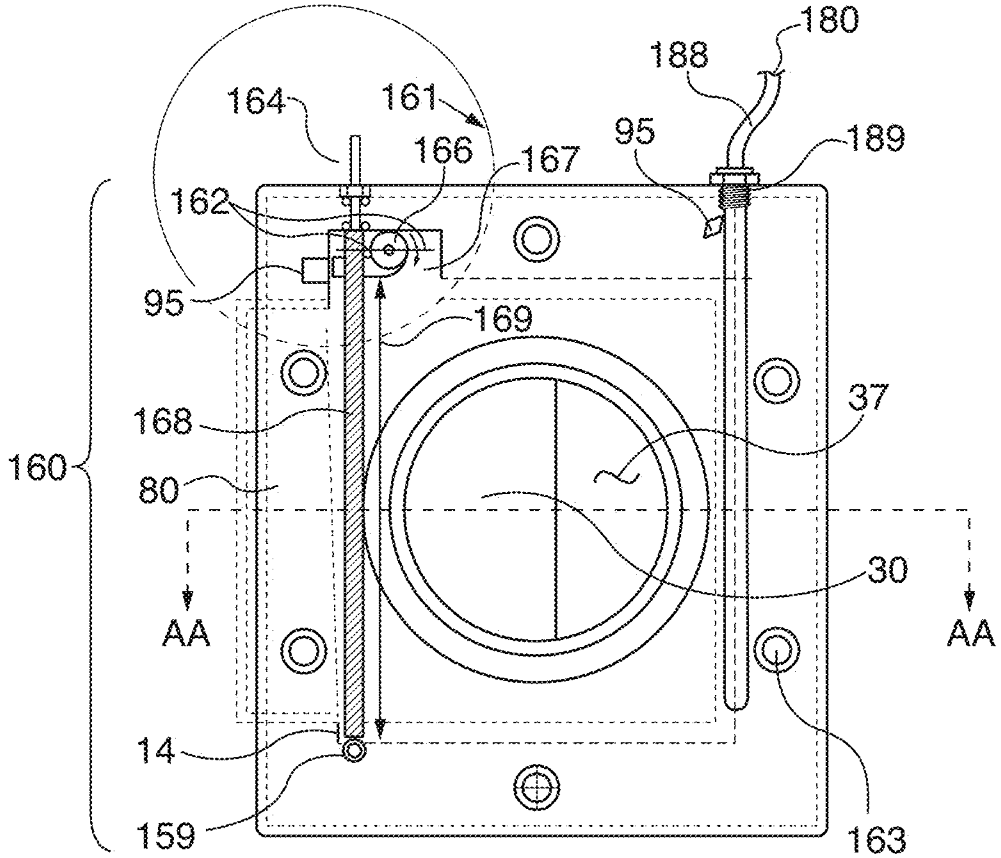
FIG. 2A shows a top view of a top portion of a sink-trap apparatus according to one aspect of the present invention.
Figure 2B:
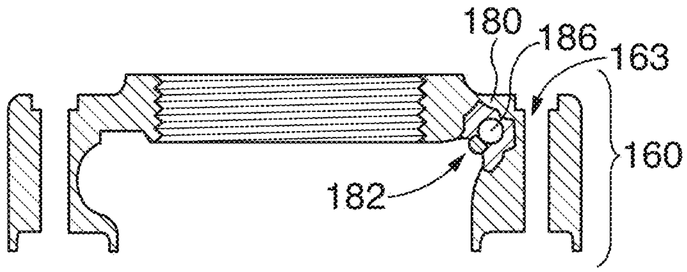
FIG. 2B shows a side sectional view of the top portion of FIG. 2A according to other aspects of the present invention.

With respect to construction, the container 12 may be aluminum or other metal construction, thin wall canister, preformed, injection molded, 3D printed plastic, resin or other suitable material. The type of fluid, the type of disinfection agent and other considerations will guide the selection of appropriate material and the applications therefor will dictate as appropriate FIGS. 2A and 2B show a container top assembly 160. Container top assembly 160 is square (as shown) and mounts to the container bulb 16. Container top assembly 160 affixes to container bulb 16 by using bolts 242 inserted into holes 163 and engaged with threaded engagement mechanism 65. Threaded engagement mechanism may be a threaded boss, or securable nuts with a washer fit.

Container top assembly 160 includes two different subassemblies as port of its structure: sprayer assembly 180 and wiper assembly 161, both for cleaning the interior of container 12. Sprayer assembly is specifically designed to spray a cleaning agent into container 12 for cleaning the inside thereof.

Sprayer assembly includes intake hose 188, connection fitting 189, spray port 186, and spray nozzles 182. Connection fitting 189 couples intake hose 188 is to spray port 186 on container top assembly 160. Spray nozzles 182 are disposed along spray port 186 and are coupled thereto. By way of construction example, the following component construction is considered in one embodiment of the present invention. Connection mechanisms for connection fitting 189 may include typical hose connectors that have an inner diameter smaller than the hose for securable disposition on the outside thereof. The connection fitting may also have a threaded male end for threadable insertion and coupling to a female threaded portion disposed at the end of spray port 186. Spray port 186 may be drilled into said container top assembly 160 to a desirable depth. Alternatively, spray port 186 may be a separate hose disposed within the container top assembly 160. The spray nozzles 182 may be threadably engaged with spray port 186 or force fit inserted using force fit nipple insertion end to the spray nozzles 182.

In operation, an external source of cleaning agent is provided to intake hose 188 and that cleaning agent flows into spray port 186 under pressure. The cleaning agent is then forced into spray port 186 and then exits into container 12 through spray nozzles 182. The purpose of the cleaning agent delivery within container 12 is to provide cleaning agent on all internal container surfaces, but specifically the surfaces of the first and second diverters 30 and 34 respectively, and interface 85. The spray that exudes from the spray nozzles 182 takes the same path as any other fluid flowing through container 12.

Wiper assembly 161 includes engagement mechanism 164, blade advancement mechanism 168, blade holder 166, blades 162 and an end 159. Engagement mechanism 164 is a connector that is external to the container 12 for connection to an external power source. Engagement mechanism 164 is connected to blade advancement mechanism 168. Blade advancement mechanism 168 is coupled to container top assembly 160 and blade holder 166 which in turn holds one or more blades 162. Strictly by way of an exemplary part specification, composition, and construction, the following arrangement may be considered in one embodiment of the present invention. Engagement mechanism 164 couples at the end for mating with a motor or a hand crank. Blade advancement mechanism 168 is a high helix shaft, the moving portion of the high helix shaft being coupled to the blade holder 166. Blade holder 166 has two slidable slots on its sides into which rubber blades 162 slide. Blade holder 166 has a complementary helix gear for mating with that of the high helix shaft and for translation of the blade holder 166 for cleaning purposes.

In operation, an external power source rotates the engagement mechanism 164 and the blade advancement mechanism 168 moves the blade holder 166 along container cleaning dimension 169. One of edge of the blade 162, or at least one edge of the multiple blades held by the blade holder 166, contacts the interface 85 at the container side of disinfection barrier 84. Another edge of blade 162, or at least one edge of the multiple blades held by the blade holder 166, contact the second diverter, containment segment 38 surface facing the disinfection volume 28. The entire assembly traverses the container 12 in container cleaning dimension 169. Upon reaching the end of the run, the power source may reverse and the wiper assembly 161 returns to the starting point. Alcove 167 may act as a starting point, that alcove being provided within container top assembly 160, and outside of the normal fluid entry volume, to house the wiper assembly 161 when not in use. The purpose of the wiping assembly is to provide a mechanical cleaning capability to the two container surfaces that are adjacent to the disinfection and across which disinfection takes place, specifically the disinfecting volume facing surfaces of the second diverter, containment segment 38 and interface 85. As stated previously, these operations may all be under computer control of computer 90.

The wiper assembly 161 and associated cleaning function are particularly important when the disinfection unit 80 is UV-based. Cleanliness of the disinfection barrier 84 at interface 85 is critical to maintaining proper function of the disinfection process by allowing the designed and required UV emission to effectively reach the disinfection volume. In the example of a UV-based, liquid, sink-trap fluid system, the wiping function may operate to both clean the interface and agitate the static fluid that exists in the both the disinfection volume and the exit volume as trap holding waste. The wiping function and associated operation of the blades 162 will agitate that trap holding waste such that the two volumes comingle and the disinfection module/UV lighting module will continue to disinfect the trap holding waste during long periods of apparatus inactivity.

It should be noted that one or both the sprayer assembly 180 and the wiper assembly 161 may be operated at any one time. Further, both are capable of computer control using computer 90 and via wiring and signaling coordinated with local controllers 95. Local controllers 95 are essentially mini-computers and include a processor and associated memory for executing stored programs locally.

Electrical power to all computers, electronics and other electrical equipment within the disinfection apparatus (10) may be supplied in any of a number of traditional manners. A standard power plug couped to the assembly is sufficient to provide external power. Alternatively, a battery installed within the disinfection apparatus (10) would also work. In any case the power supply is electrically connected and mechanically coupled to a power module that creates and conditions the proper voltages and current supplies to power each of the electrical components within the disinfection apparatus (10). In the case of external power, the power module may be a plug in adapter that operates off standard 120 v building electrical outlets. In the case of an included battery, the apparatus may also include a circuit module to provide and condition the appropriate power level.

Figure 3:
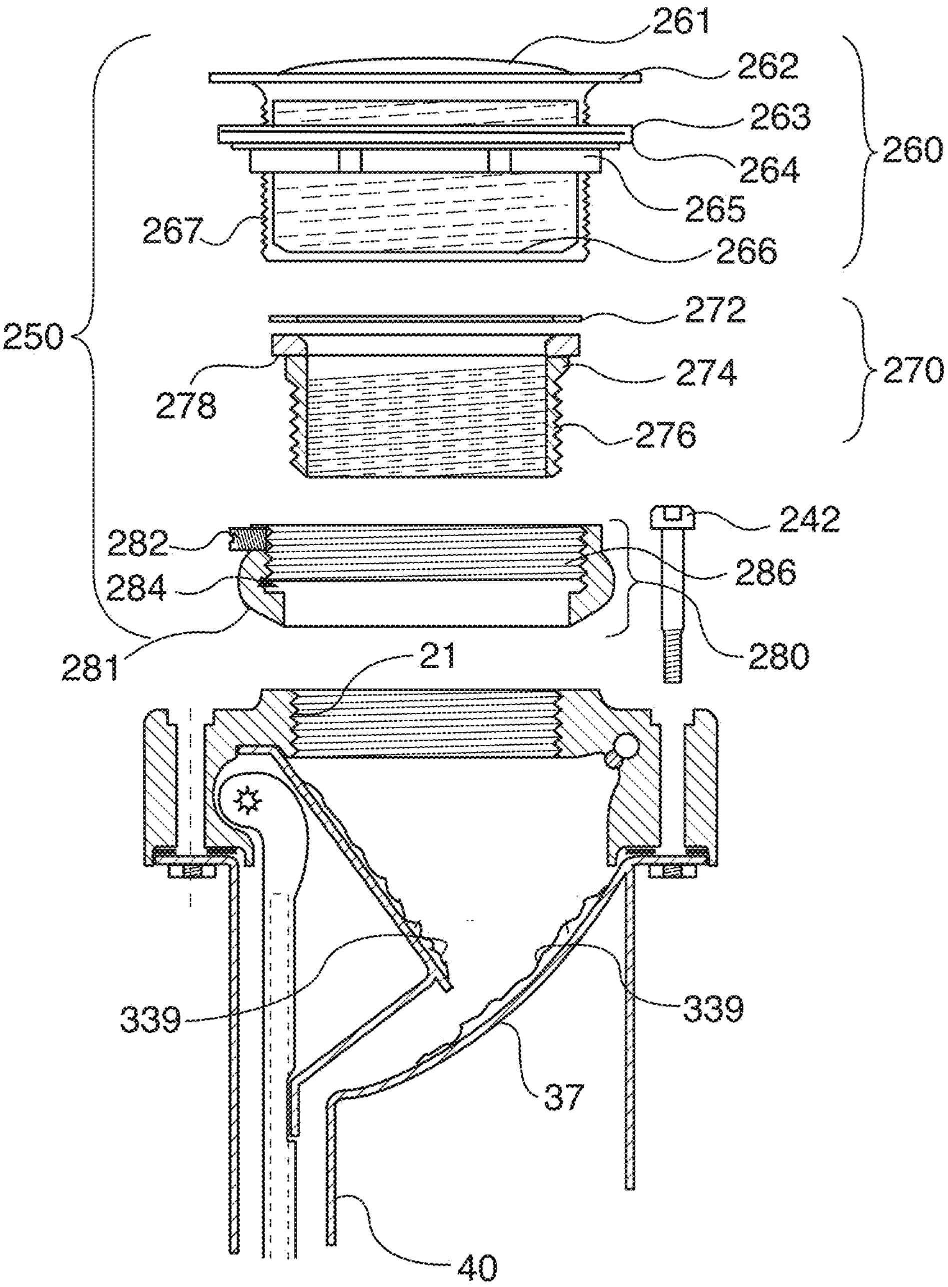
FIG. 3 shows a side sectional assembly drawing of the sink-trap, and drain elements associated with the same, according to one aspect of the present invention.
Figure 4A:
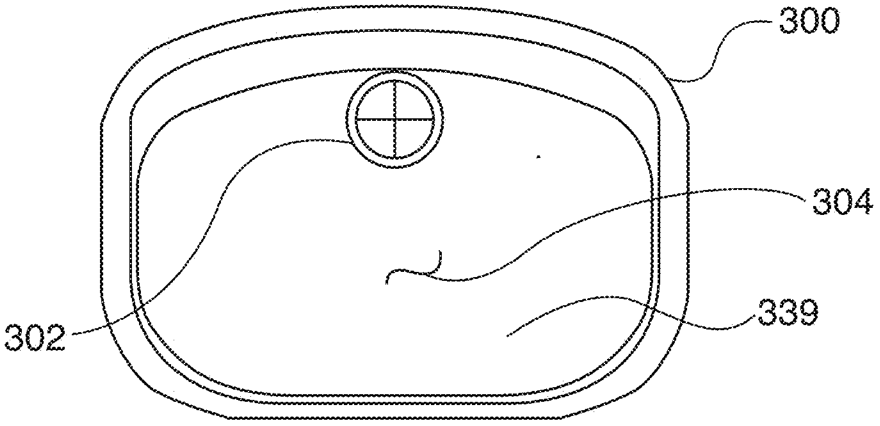
FIG. 4A shows a top view of a sink associated with the sink trap, according to one aspect of the invention.

FIGS. 3 and 4A show a drain assembly 250 and a sink 300 for use with disinfection apparatus 10 which is a sink-trap in this embodiment. Referring to FIG. 3, drain assembly 250 includes upper drain assembly 260, spud assembly 270 and flange nut 280. Upper drain section includes strainer 261, top rim 262, compression washer 263, fiber slip washer 264, threaded lock ring 265 and safety strainer 266. Portions of upper drain assembly 260 are configured and dimensioned for insertion through drain hole 302 in sink 300. Strainer 261 is above the sink floor and top rim 262 provides a seating flange for resting on inner sink surface 304.

In assembly, strainer 261 is inserted through drain hole 302. Compression washer 263 and fiber slip washer 264 slide over threaded portion 267 and are secured by threaded engagement to the threaded portion of upper drain section from underneath the sink using threaded lock ring 265 to secure the upper drain assembly 260 to the sink.

Strainer 261 is convex to provide a roll-off function for solid particulate matter introduced in the sink. Strainer 261 is removeable for cleaning out the upper drain section. Strainer 261 and safety strainer 266 can employ different size strainer holes so that larger material will pass through removeable strainer 261 only to be stopped by safety strainer 266. This double strainer system prevents larger particulate matter from entering the disinfection apparatus 10 and allows for the most effective disinfection of the liquid therein.

Spud assembly 270 includes water seal washer 272 and flange spud 274. Threaded portion 276 up to rim 278 are sized to fit within and through the hole within flange nut 280 and mate with threaded portion 21 at the top of container 12.

Flange nut 280 includes threaded portion 286. Threaded portion 286 is sized and mated with threaded portion 267 at the bottom of upper drain assembly 260.

In assembly, spud assembly is inserted within flange nut 280 until rim 278 rests on ledge 284 in flange nut 280. Mated threaded portion 276 is screwed into threaded portion 21 of the disinfection apparatus 10 so that flange nut is secured to the top of the same. The entire apparatus including the spud assembly and the flange nut are then lifted and threaded portion 286 of flange nut 280 is secured by threaded engagement to the threaded portion 267 of the upper drain assembly 260. Set screw 282 may be included as part of flange nut 280 to secure spud assembly 270 within the flange nut 280. The use of the flange nut permits the removal of the container 12 without having to remove the top drain assemblies. The assembly steps of the overall installation may be rearranged for the efficiency of installation.

Figure 4B:
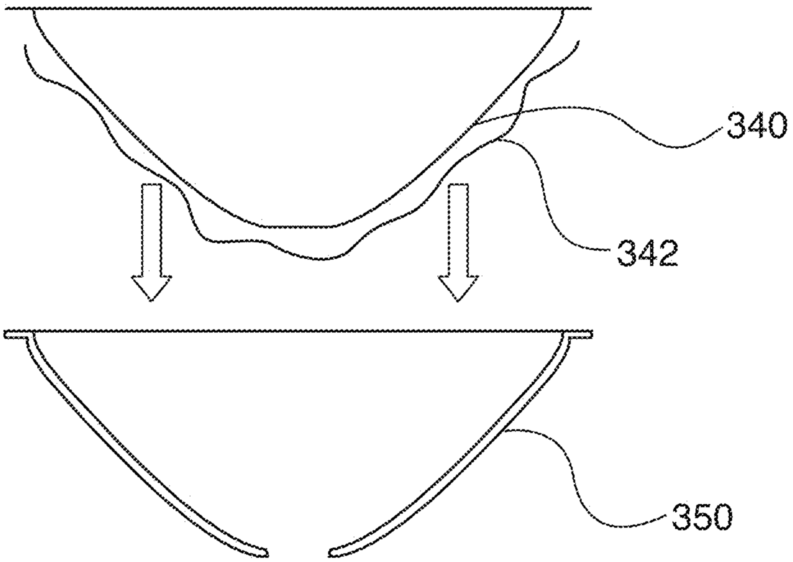
FIG. 4B shows the side sectional views of the sink and sink filter, both associated with the sink trap, according to one aspect of the present invention.

Referring to FIGS. 4A and 4B, a sink 300 is provide having a drain hole 302 an inner sink surface 304 and a sink contour 350. The inner sink surface 304 may be laser trimmed or coated as described above with respect the diverters so as to minimize splash. Alternatively, sink liner 340 having a sink liner contour 342 may be provided to accommodate splash resistance. Sink liner contour 342 is designed to match sink contour 350 for seamless insertion and aesthetic appeal. Sink liner 340 may be of any porous material or other material that minimizes splash. Sink liner 340 may be a once-used product, for hospital use for example. Sink liner 340 may also be a more durable, washable composition, e.g. cotton, pulp or synthetic blend material for longer term durability and use in the home, for example. Sink liner 340 may also be pretreated with anti-pathogen disinfectant to enhance the function thereof in reducing the spread of disease.

The sink design itself would ideally provide form splash reduction The sinks will meet Facility Guidelines Institute (FGI) regulations for hand-washing stations: Sinks should be constructed of non-porous materials with deep basins and be at least 144 square inches. The sinks of the present invention are envisioned to have some standardized features. For example, they would ideally have vertical sides that are between 75° to 90° off of a horizontal line before they transition to 45° at the drain opening. The general shape and size can vary as long as 144 square inches in volume is achieved and the water impact angle is greater than 45° to reduce aerosolization, atomization and corona splash.

It should be appreciated that many of the parts of the present invention are replaceable and snap-on or screw in attachable for ease of replacement, change out or maintenance. In particular disinfection unit 80 may be snap on replaceable. Different units may be attached having different UV or other optical lighting apparatus or even changing to a sprayer disinfectant. Certain replacements of this component would also necessitate a change in the disinfection barrier 84 which may be slide out say with a channel system and rubber sealant/gasket arrangement. Further, the disinfection module, associated lights/sprayers, all plumbing, electrical computer 90 control and data interface etc. may be replaceable within the disinfection unit 80. Wiper blade(s) 62, all connection fittings and assemblies are removeable for maintenance and replacement.

Figure 5A:
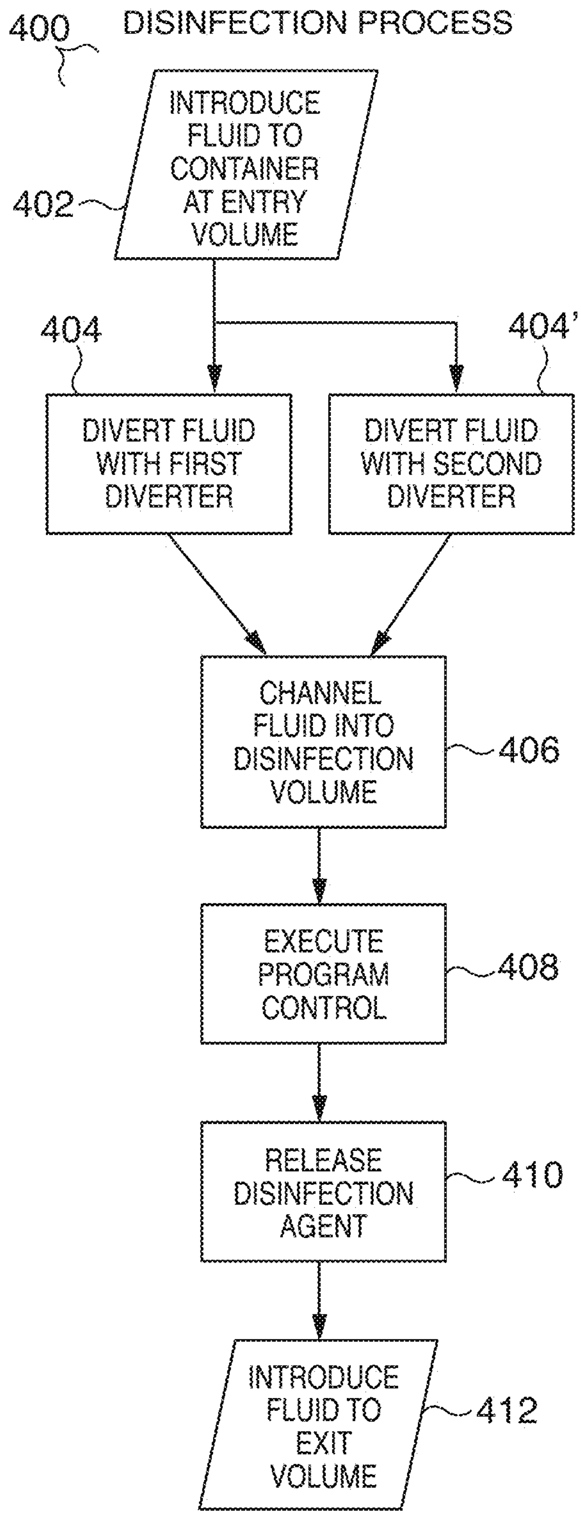
FIG. 5A shows a process flow for the disinfection of the sink trap, according to one aspect of the present invention.

Referring to FIG. 5A, a process flow is shown a disinfection process 400 and computer instructions executing the same. The process starts by introducing 402 the fluid into the container 12 at the fluid entry volume 26. The next two steps occurring in parallel for the most part are diverting the fluid 404 with the first diverter 30 and diverting the fluid 404' with the second diverter 34. The process continues with the step of channeling the fluid 406 into the disinfection volume 28. Then program controls are executed 408 by the computer 90 and transmitted over control and data interface 96 to cause the disinfection module 82 to release 410 disinfection agent 88 into the disinfection volume 28. The disinfection process concludes with the introduction of the fluid 412 into the fluid exit volume 29 for evacuation from the container 12.

Figure 5B:
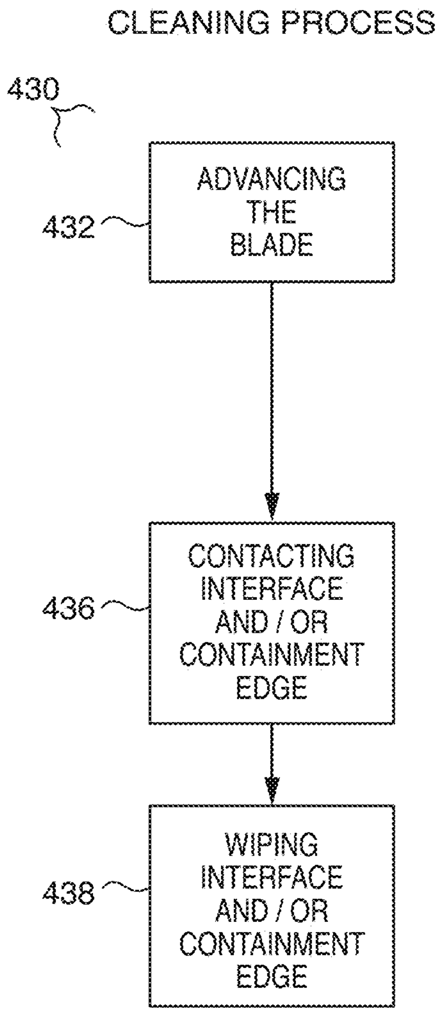
FIG. 5B shows an additional process flow for the cleaning of the sink trap according to another aspect of the present invention.

Referring to FIG. 5B, a sub-process flow is shown for a cleaning process 430 and computer instructions for executing the same. This process can be performed under computer control at the system designer's discretion. The process starts by advancing 432 the blade 162 in a container cleaning dimension 169 with the blade advancement mechanism 168. Contact is made 436 by the blade 162 with interface 85 and/or the surface of the second diverter, containment segment 38. The process is complete with the wiping 438 of interface 85 and/or the surface of the second diverter, containment segment 38.

It is to be understood that the computerized aspects of the present invention may be implemented in various forms of hardware, software, firmware, special purpose processors, or a combination thereof. Preferably, the computer portions of the present invention are implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device.

It is to be understood that, because some of the constituent system components and method steps depicted in the accompanying figures are preferably implemented in software, the actual connections between the system components (or the process steps) may differ depending upon the manner in which the present invention is programmed. Specifically, any of the computers or devices may be interconnected using any existing or later-discovered networking technology and may also all be connected through a lager network system, such as a corporate network, metropolitan network or a global network, such as the internet.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, rather this disclosure is to be understood in the broadest sense allowable by law.

Although various embodiments, which incorporate the teachings of the present invention have been shown and described in detail herein, those skilled in the art can readily devise many other varied embodiments that still incorporate these teachings.

What is claimed is:

1. A disinfection apparatus for disinfecting fluid flowing through said disinfection apparatus, said apparatus comprising:

a container having a fluid entry opening, a fluid exit opening, a disinfection volume between said fluid entry and exit openings, at least one rigid fluid diverter disposed within said disinfection volume, said rigid fluid diverter conditioning the fluid flowing through said disinfection volume to cause the fluid flow to be more uniform, said container having a disinfection unit coupled to said container, said disinfection unit including a disinfection module, a disinfection barrier and a computer, said computer coupled to said disinfection module through a control and data interface, said computer including a processor and an associated memory coupled to said processor, said processor executing program instructions within said memory to activate control signals within said control and data interface, said disinfection barrier providing an interface between said disinfection unit and said container, said interface providing access to said disinfection volume for said disinfection module, said disinfection module releasing a disinfection agent into said disinfection volume under the control of said computer, said disinfection agent disinfecting the uniformly conditioned fluid as the fluid passes through said disinfection volume.

2. The apparatus of claim 1 further comprising a sensor, said sensor coupled to said computer with said control and data interface, said sensor including sensor leads disposed within said disinfection volume.

3. The apparatus of claim 2 wherein said sensor leads sense a characteristic of the fluid and return fluid data signals representative of said characteristic to said computer.

4. The apparatus of claim 3 wherein said characteristic is one of toxicity, Ph, a particular contaminant, salinity, or the presence of liquid in the fluid.

5. The apparatus of claim 4 wherein said computer performs a control function regarding said disinfection agent based on said sensed characteristic.

6. The apparatus of claim 5 wherein said control function is controlling one of a disinfection duration, a disinfection strength, a disinfection cycle or the selection of a disinfection agent.

7. The apparatus of claim 6 wherein said disinfection agent is UV light and the selection of a disinfection agent is a selection of a particular UV wavelength.

8. The apparatus of claim 3 wherein said computer monitors a status of a disinfection process in response to said returned fluid data signals.

9. The apparatus of claim 1 wherein said disinfection barrier includes a spray module, said disinfection unit includes a disinfectant chemical contained within said disinfection module, said disinfectant chemical being said disinfection agent.

10. The apparatus of claim 1 wherein said disinfection barrier includes an optical barrier, said disinfection unit includes at least one UV light, said UV radiation emitted from said UV light being said disinfection agent.

11. The apparatus of claim 10 further comprising a baffle coupled to said container, said baffle substantially contains said UV light and prevents said UV light from exiting said container at said fluid entry opening.

12. The apparatus of claim 1 wherein said at least one diverter includes a coating, said coating further conditioning the flow of the fluid.

13. The apparatus of claim 1 wherein said container is vertically oriented with respect to gravity, said at least one diverter includes a drip edge, said drip edge further conditioning the flow of the fluid.

14. A method of disinfecting a fluid within a container, said container including at least one fluid diverter within said container, said container including a disinfection volume and a disinfection unit coupled to said container, said disinfection unit including a disinfection module, a disinfection barrier and a computer, said computer coupled to said disinfection module through a control and data interface, said computer including a processor and an associated memory coupled to said processor, said memory containing program instructions for execution by said processor, said program instructions activating control signals within said control and data interface, said method comprising:

conditioning the fluid with said at least one diverter to provide a uniformly conditioned fluid to said disinfection volume;

executing program instructions by said processor to activate control signals within said control and data interface, and releasing a disinfection agent from said disinfection module under program control, said disinfection agent being delivered to said disinfection volume through said disinfection barrier, said disinfection barrier providing an interface between said disinfection unit and said disinfection volume, said disinfection agent disinfecting the fluid.

15. The method of claim 14 further comprising:

sensing a characteristic of the fluid with a sensor, said sensor coupled to said computer with said control and data interface, said sensor including sensor leads disposed within a disinfection volume within said container; and returning fluid data signals representative of said characteristic to said computer.

16. The method of claim 15 further comprising:

performing control functions based on said sensed characteristic, said control function controlling one of a disinfection duration, a disinfection strength, or a disinfection cycle.

17. The method of claim 15 further comprising:

selecting a disinfection agent based on said returned fluid data signals.

18. The method of claim 17 wherein said disinfection agent is UV light and said step of selecting includes the step of selecting a UV wavelength among several based on said fluid data.

19. The method of claim 15 further comprising:

monitoring a status of a disinfection process using said returned fluid data signals.

20. A non-transitory, machine-readable storage media having executable instructions causing a processor within a of computer to perform a method for disinfecting a fluid within a container, said container including at least one fluid diverter within said container, said container including a disinfection volume and a disinfection unit coupled to said container, said disinfection unit including a disinfection module, a disinfection barrier and a computer, said computer coupled to said disinfection module through a control and data interface, said computer including a processor and an associated memory coupled to said processor, said memory containing program instructions for execution by said processor, said program instructions activating control signals within said control and data interface, said machine-readable storage media having steps for performing the method of:

conditioning the fluid with said at least one diverter to provide a uniformly conditioned fluid to said disinfection volume;

executing program instructions by said processor to activate control signals within said control and data interface, and releasing a disinfection agent from said disinfection module under program control, said disinfection agent being delivered to said disinfection volume through said disinfection barrier, said disinfection barrier providing an interface between said disinfection unit and said disinfection volume, said disinfection agent disinfecting the fluid.

* * * * *